United States Patent
Schwab et al.

(10) Patent No.: US 10,603,477 B2
(45) Date of Patent: Mar. 31, 2020

(54) DISSOLVABLE MICRONEEDLES FOR SKIN TREATMENT

(71) Applicant: Allergan, Inc., Irvine, CA (US)

(72) Inventors: Justin J. Schwab, San Francisco, CA (US); Michael Augarten, Irvine, CA (US); Zachary Dominguez, Santa Barbara, CA (US); Ethan Franklin, Goleta, CA (US); Edwin J. Kayda, Santa Barbara, CA (US); Jason Metzner, Covington, WA (US)

(73) Assignee: Allergan, Inc., Irvine, CA (US)

(*) Notice: Subject to any disclaimer, the term of this patent is extended or adjusted under 35 U.S.C. 154(b) by 9 days.

(21) Appl. No.: 15/903,262

(22) Filed: Feb. 23, 2018

(65) Prior Publication Data

US 2018/0229017 A1 Aug. 16, 2018

Related U.S. Application Data

(63) Continuation of application No. 14/671,690, filed on Mar. 27, 2015, now abandoned.

(60) Provisional application No. 61/972,165, filed on Mar. 28, 2014.

(51) Int. Cl.
| | |
|---|---|
| *A61M 37/00* | (2006.01) |
| *A61L 31/04* | (2006.01) |
| *A61L 31/14* | (2006.01) |
| *A61L 31/16* | (2006.01) |

(52) U.S. Cl.
CPC ....... *A61M 37/0015* (2013.01); *A61L 31/042* (2013.01); *A61L 31/148* (2013.01); *A61L 31/16* (2013.01); *A61L 2300/414* (2013.01); *A61L 2300/428* (2013.01); *A61M 2037/0023* (2013.01); *A61M 2037/0046* (2013.01); *A61M 2037/0061* (2013.01)

(58) Field of Classification Search
CPC .................................. A61M 37/0015
See application file for complete search history.

(56) References Cited

U.S. PATENT DOCUMENTS

| | | | |
|---|---|---|---|
| 5,586,466 | A | 12/1996 | Feigner et al. |
| 6,334,856 | B1 | 1/2002 | Allen et al. |
| 6,440,096 | B1 | 8/2002 | Lastovich |
| 6,503,231 | B1 | 1/2003 | Prausnitz et al. |
| 6,537,264 | B1 | 3/2003 | Cormier et al. |

(Continued)

FOREIGN PATENT DOCUMENTS

| | | |
|---|---|---|
| CA | 2594291 | 7/2006 |
| CA | 2686093 | 10/2008 |

(Continued)

OTHER PUBLICATIONS

International Search Report and Written Opinion from PCT/US2018/000046, dated Jun. 7, 2018, 17 pages.

(Continued)

*Primary Examiner* — Benjamin J Packard
(74) *Attorney, Agent, or Firm* — Nathan S. Smith; Kalpesh V. Upadhye; Morgan, Lewis & Bockius LLP

(57) ABSTRACT

A skin treatment device is provided including bioerodible polymeric microneedles which are designed to more effectively deliver beneficial agents to the skin. The device includes a flexible substrate and an arrangement, for example, an array, of microneedles projecting from the substrate.

20 Claims, 6 Drawing Sheets

(56) References Cited

U.S. PATENT DOCUMENTS

| | | | |
|---|---|---|---|
| 6,565,532 B1 | 5/2003 | Yuzhakov et al. | |
| 6,611,707 B1 | 8/2003 | Prausnitz et al. | |
| 6,623,457 B1 | 9/2003 | Rosenberg | |
| 6,689,100 B2 | 2/2004 | Connelly et al. | |
| 6,743,211 B1 | 6/2004 | Prausnitz et al. | |
| 6,946,501 B2 | 9/2005 | Kovachar | |
| 7,226,439 B2 | 6/2007 | Prausnitz et al. | |
| 7,416,541 B2 | 8/2008 | Yuzhakov et al. | |
| 8,366,677 B2 | 2/2013 | Kaspar et al. | |
| 8,476,243 B2 | 7/2013 | Kaspar et al. | |
| 9,987,361 B1 | 6/2018 | Suzuki | |
| 2002/0111600 A1 | 8/2002 | Cormier et al. | |
| 2002/0138049 A1* | 9/2002 | Allen | A61B 5/14514 604/272 |
| 2003/0069548 A1 | 4/2003 | Connelly et al. | |
| 2003/0167556 A1 | 9/2003 | Kelley | |
| 2004/0009180 A1 | 1/2004 | Donovan | |
| 2004/0049150 A1 | 3/2004 | Dalton et al. | |
| 2005/0065463 A1 | 3/2005 | Tobinaga et al. | |
| 2005/0197308 A1 | 9/2005 | Dalton et al. | |
| 2005/0209565 A1 | 9/2005 | Yuzhakov et al. | |
| 2005/0261632 A1 | 11/2005 | Xu | |
| 2006/0057165 A1 | 3/2006 | Dimitrakoudis et al. | |
| 2006/0100584 A1 | 5/2006 | Olejnik et al. | |
| 2006/0127465 A1 | 6/2006 | Maeonsono Etal | |
| 2007/0009587 A1 | 1/2007 | Daddona | |
| 2007/0049901 A1 | 3/2007 | Wu et al. | |
| 2007/0060867 A1 | 3/2007 | Xu | |
| 2008/0009811 A1 | 1/2008 | Cantor | |
| 2008/0125743 A1 | 5/2008 | Yuzhakov | |
| 2008/0269666 A1 | 10/2008 | Wang et al. | |
| 2008/0269685 A1 | 10/2008 | Singh et al. | |
| 2009/0043279 A1 | 2/2009 | Kaspar et al. | |
| 2009/0099502 A1 | 4/2009 | Tokumoto et al. | |
| 2009/0131905 A1 | 5/2009 | Allen et al. | |
| 2009/0182306 A1 | 7/2009 | Lee et al. | |
| 2010/0196445 A1 | 8/2010 | David | |
| 2010/0221314 A1 | 9/2010 | Matsudo et al. | |
| 2010/0228203 A1 | 9/2010 | Quan et al. | |
| 2010/0280457 A1 | 11/2010 | Tokumoto et al. | |
| 2011/0028905 A1 | 2/2011 | Takada | |
| 2011/0098651 A1 | 4/2011 | Falo, Jr. et al. | |
| 2011/0121486 A1 | 5/2011 | Oh et al. | |
| 2011/0152792 A1* | 6/2011 | Takada | A61M 37/0015 604/272 |
| 2011/0190688 A1 | 8/2011 | Tagliaferri et al. | |
| 2011/0195124 A1 | 8/2011 | Jin | |
| 2011/0270221 A1 | 11/2011 | Ross | |
| 2012/0004614 A1 | 1/2012 | Stumber | |
| 2012/0027810 A1 | 2/2012 | Chen et al. | |
| 2012/0029434 A1 | 2/2012 | Kobayashi | |
| 2012/0150023 A1 | 6/2012 | Kaspar et al. | |
| 2012/0193840 A1 | 8/2012 | Kwon | |
| 2012/0220981 A1 | 8/2012 | Soo et al. | |
| 2012/0283695 A1 | 11/2012 | Chen et al. | |
| 2013/0012882 A1 | 1/2013 | Quan et al. | |
| 2013/0072902 A1 | 3/2013 | Takada et al. | |
| 2013/0078874 A1 | 3/2013 | Tokumoto et al. | |
| 2013/0096532 A1 | 4/2013 | Ozel et al. | |
| 2014/0276362 A1 | 9/2014 | Alvarez | |
| 2014/0276378 A1 | 9/2014 | Chen et al. | |
| 2015/0196359 A1 | 7/2015 | Paithankar | |
| 2015/0209563 A1 | 7/2015 | Amir | |
| 2015/0238527 A1 | 8/2015 | Chang | |
| 2015/0297688 A1 | 10/2015 | Borodic | |

FOREIGN PATENT DOCUMENTS

| | | |
|---|---|---|
| CA | 2698632 | 12/2010 |
| EP | 1632263 | 3/2008 |
| EP | 2213284 | 8/2010 |
| JP | 2003-238347 | 8/2003 |
| JP | 2005-272398 | 10/2005 |
| JP | 2009-201956 | 9/2009 |
| JP | 2009-254756 | 11/2009 |
| JP | 2010-082401 | 4/2010 |
| JP | 2011-167486 | 9/2011 |
| JP | 2012-025723 | 2/2012 |
| JP | 2012-031177 | 2/2012 |
| JP | 2012-041329 | 3/2012 |
| JP | 2013-009960 | 1/2013 |
| JP | 2013-032324 | 2/2013 |
| JP | 2013-052202 | 3/2013 |
| JP | 2013-075165 | 4/2013 |
| KR | 10-2007-0018410 | 2/2007 |
| WO | WO 99/64580 | 12/1999 |
| WO | WO 00/44438 | 8/2000 |
| WO | WO 02/064193 | 8/2002 |
| WO | WO 2006/018642 | 2/2006 |
| WO | WO 2006/077742 | 7/2006 |
| WO | WO 2006/131931 | 12/2006 |
| WO | WO 2008/010681 | 1/2008 |
| WO | WO 2008/130587 | 10/2008 |
| WO | WO 2008/139786 | 11/2008 |
| WO | WO 2009/021048 | 2/2009 |
| WO | WO 2009/94394 | 7/2009 |
| WO | WO 2010/056922 | 5/2010 |
| WO | WO 2010/078323 | 7/2010 |
| WO | WO 2011/044367 | 4/2011 |
| WO | WO 2011/115272 | 9/2011 |
| WO | WO 2012/023044 | 2/2012 |
| WO | WO 2012/115207 | 8/2012 |
| WO | WO 2012/122162 | 9/2012 |
| WO | WO 2012/122163 | 9/2012 |
| WO | WO 2012/128363 | 9/2012 |
| WO | WO 2012/153266 | 11/2012 |
| WO | WO 2013/57819 | 4/2013 |
| WO | WO 2013/096206 | 6/2013 |
| WO | WO 2014/041531 | 3/2014 |

OTHER PUBLICATIONS

Hiraishi et al., "Performance and characteristics evaluation of a sodium hyaluronate-based microneedle patch for a transcutaneous drug delivery system," International Journal of Pharmaceutics, 2013, vol. 441, pp. 570-579.

Motokawa et al., "Selectively crosslinked hyaluronic acid hydrogels for sustained release formulation of erythropoietin," Journal of Biomedical Materials Research, Part A, May 2006, 7 pages.

Australian Exam Report No. 1 from Australian Patent Application No. 2015237230, dated May 13, 2019, 4 pages.

European Office Action from European Patent Application No. 15716319.7, dated Nov. 8, 2017, 7 pages.

Bariya et al., Microneedles: an emerging transdermal drug delivery system, Journal of Pharmacy and Pharmacology, 2011, pp. 11-29.

Cormier et al., "Transdermal delivery of desmopressin using a coated microneedle array patch system," Journal of Controlled Release, 2004, vol. 97, pp. 503-511.

Donnelly et al., "Microneedle-based drug delivery systems: Microfabrication, drug delivery and safety," Drug Delivery, 2010, 17(4), pp. 187-207.

Gonzalez-Gonzalez et al.; Silencing of Reporter Gene Expression in Skin Using siRNAs Delivered by a Soluble Protrusion Array Device(PAD); Molecular Therapy; Sep. 2010; pp. 167-1674; vol. 18.

Lee et al, "Drawing lithography: three-dimensional fabrication of an ultrahigh-aspect-ratio microneedle," Advanced Materials, Jan. 2010, 22(4), pp. 483-486.

Li et al., "An optimized hollow microneedle for minimally invasive blood extraction," Biomedical Microdevices, Jul. 2012, 15(1), pp. 17-25.

Park et al., "Biodegradable polymer microneedles: Fabrication, mechanics and transdermal drug delivery," Journal of Controlled Release, vol. 104, No. 1, May 2005, pp. 51-66.

Prausnitz, "Microneedles for transdermal drug delivery," Advanced Drug Delivery Reviews. 2004, vol. 56, pp. 581-587.

Schmid, "Microneedles May Take the Ouch Out of Flue Shots, Researchers Developing Skin Patch for Influenza Vaccine," msnbc.com; http://www.msnbc.msn.com/id/38301183/from/toolbar; Jul. 18, 2010.

(56) References Cited

OTHER PUBLICATIONS

Shiseido News Release, The IFSCC Conference 2011, Development of self-dissolving microneedles consisting of hyaluronic acid as an anti-wrinkle treatment.

Wang et al., "Recent Advances in the design of polymeric microneedles for transdermal drug delivery and biosensing," Lab on a Chip, Mar. 2017, 17(8), pp. 1373-1387.

* cited by examiner

DISSOLVABLE MICRONEEDLES FOR SKIN TREATMENT

This application is a continuation of U.S. patent application Ser. No. 14/671,690, filed on Mar. 27, 2015, which claims priority to and the benefit of U.S. Provisional Patent Application No. 61/972,165, filed on Mar. 28, 2014, the entire disclosure of each of these applications being incorporated herein by this specific reference.

The present invention generally relates to skin treatment and rejuvenation, and more specifically relates to a skin treatment device including polymeric microneedles, and methods of treating skin using these devices.

BACKGROUND

Human dermis is a layer of skin between the epidermis and subcutaneous tissue. The epidermis, serves as a barrier to protect the body against microbial pathogens, oxidant stress (UV light), water loss and chemical compounds, and provides mechanical resistance. The subcutaneous tissue consists of connective tissue and functions as a cushion for the body from stress and strain. The dermis is tightly connected to the epidermis through a basement membrane. Structural components of the dermis are collagen, elastic fibers, glycosaminoglycan, and extra fibrillar matrix. The glycosaminoglycan, e.g. hyaluronan, has multiple functions such as, to ensure good hydration, to assist in the organization of the extracellular matrix (ECM), to act as a filler material, and to participate in tissue repair mechanisms. The extracellular matrix plays an important role in skin aging: in young skin, the collagen fibers form a three-dimensional network. The fibroblasts bind to collagen fibrils via multiple contact sites (integrins) on their surface. This binding builds up a tensile stress, which balances the synthesis of collagen and collagen-degrading matrix-metalloproteins in the fibroblasts. In aged skin, the structure of the extracellular matrix is damaged by collagen breakdown—partial fragmentation of the collagen.

Skin aging is a progressive phenomenon, occurs over time and can be affected by lifestyle factors, such as alcohol consumption, tobacco and sun exposure. Aging of the facial skin can be characterized by atrophy, slackening, and fattening. Atrophy corresponds to a massive reduction of the thickness of skin tissue. Slackening of the subcutaneous tissues leads to an excess of skin and ptosis and leads to the appearance of drooping cheeks and eye lids. Fattening refers to an increase in excess weight by swelling of the bottom of the face and neck. These changes are typically associated with dryness, loss of elasticity, and rough texture.

To improve cell function of skin, there are two main approaches: one is to supply skin cells with essential building blocks through oral nutrition and supplements or topical creams and serums or vigorous daily exercise to increase blood-flow and encourage the lymphatic system; the other approach relates to optimizing release of growth factors, i.e. substances that cause cells to differentiate, proliferate and/or grow, and cytokines which signal molecules released by cells to communicate with other cells. However, applying active ingredients topically to skin in order to improve cell function has generally not been highly effective, likely due to the impermeable nature of stratum corneum and other superficial layers of the epidermis.

Non-invasive or low-invasive techniques and devices for facilitating delivery of beneficial agents into skin have been proposed. For example, microneedle devices have been used to create numerous shallow punctures in the dermis, with the goal of enabling better penetration of topical compositions into the punctured skin. Such microneedle devices are used to perforate the skin and topical compositions are then sometimes applied to the punctured skin.

There remains an unmet need for better methods, devices and treatments for improving skin conditions, for example, in order to optimize skin health and improve outward appearance.

SUMMARY

The present invention provides methods, devices and treatments for benefitting skin, for example, by enhancing penetration of skin for more effective delivery of drugs, pharmaceuticals, antioxidants, vitamins, and other beneficial agents.

In one embodiment, a skin treatment device is provided. The device may include microneedles which are designed to more effectively deliver beneficial agents to the skin. The device may comprise a substrate, and an arrangement, for example, an array of microneedles projecting from the substrate. The microneedles may be comprised of a biodegradable polymer, for example, a polysaccharide, for example, hyaluronic acid. The microneedles may further include an additive, for example, a vitamin or other beneficial agent.

The device is preferably designed such that the arrangement of microneedles will facilitate penetration of the microneedles into the skin, for example into the stratum corneum, when the device is applied to the skin. For example, in some embodiments, the arrangement of microneedles comprises microneedles having different lengths from one another. For example, the array may comprise alternating first and second microneedles, wherein the first microneedles have a first length and second microneedles have a second length different from the first length.

In some embodiments, the device may include a first region sized and/or shaped to cover a first portion of skin to be treated, and a second region adjacent and connected to the first region, the second region sized and/or shaped to cover a second portion of skin to be treated. In some embodiments, the first region includes first microneedles projecting from the substrate and having a first length, and the second region includes second microneedles projecting from the substrate and having a second length, different from the first length, projecting from the first region and second microneedles having a second height different from the first height, projecting from the second region.

Methods of treating skin are also provided. In one embodiment, a method of treating skin comprises the step of facilitating penetration of microneedles into skin by drawing an area of skin to be treated toward an array of microneedles, for example using suction or a vacuum.

In yet another aspect of the invention, a skin treatment assembly is provided comprising a first patch having a first shape for covering a portion of a face to be treated and including a first array of microneedles and a second patch having a second shape different from the first shape for covering another portion of a face to be treated and including a second array of microneedles different from the first array.

In some embodiments, the first array comprises microneedles having a first length and the second array comprises microneedles having a second length different from the first length. In other embodiments, the first array comprises microneedles having a first spacing and the second array comprises microneedles having a second spacing different from the first spacing.

BRIEF DESCRIPTION OF THE DRAWINGS

The present invention may be more readily understood and/or the advantages thereof better appreciated by considering the following Detailed Description and accompanying drawings of which.

DETAILED DESCRIPTION

Figure 1:
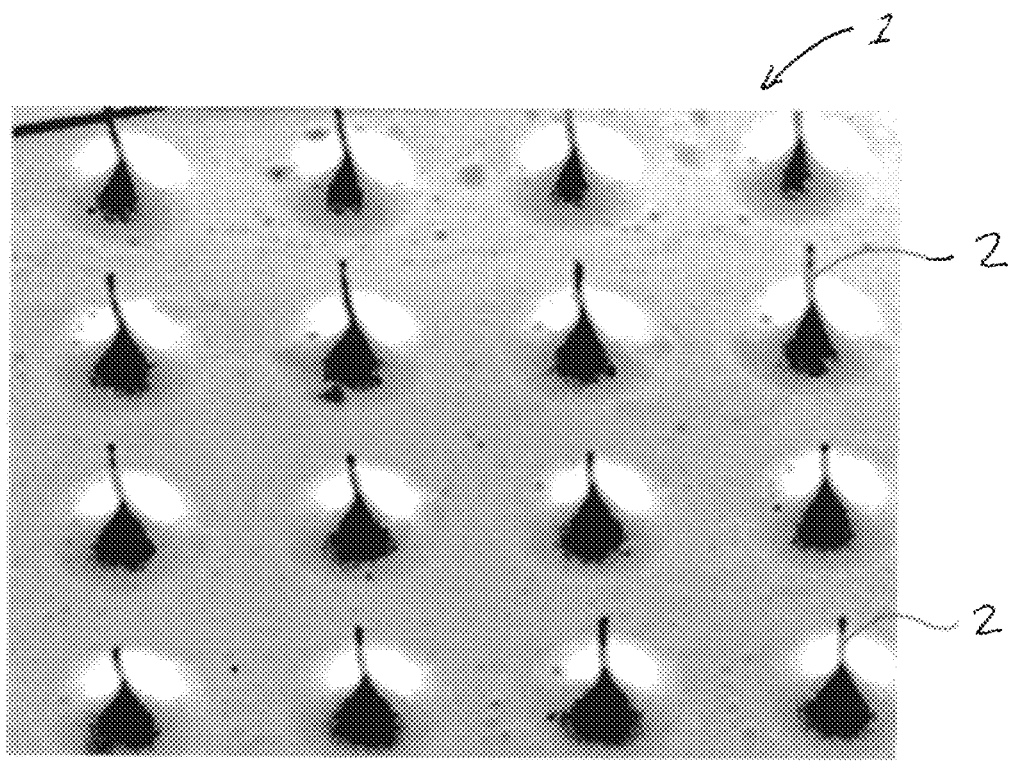
FIG. 1 shows an SEM image of a portion of a PRIOR ART microneedle device.
Figure 2A:
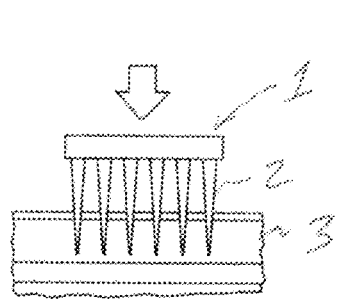
FIGS. 2a-2c illustrate, in simplified form, the mechanism of action of the PRIOR ART microneedle device shown in FIG. 1.
Figure 2B:
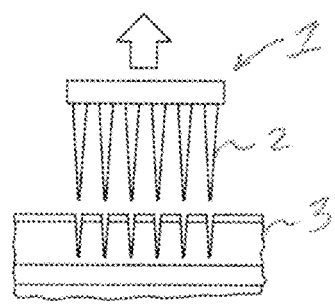
Figure 2C:
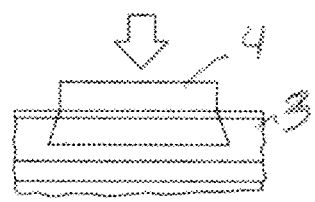

Turning to FIG. 1, a SEM image of a portion of a PRIOR ART microneedle device 1 is shown. The microneedles 2 have a uniform length, shape and spacing. As illustrated in FIG. 2a through 2c, the microneedles 2 are generally used to prick or penetrate skin 3 at very superficial, shallow depths (FIG. 2a), to mechanically make the skin 3 more porous (FIG. 2b) and, theoretically, to permit penetration of topical agents 4 into the deeper layers of the skin (FIG. 2c).

In accordance with the present invention, polymeric microneedles, and arrays of such microneedles, coupled with both simple and complex geometries and arrangements, have been developed for more effectively delivering pharmaceuticals, drugs, and other beneficial agents to skin. Delivery of such agents and ingredients may enhance the look and feel of the skin, by promoting hydration and improving skin texture and elasticity.

In one aspect of the invention, the microneedles comprise a biocompatible polymeric material. In some embodiments, the microneedles comprise a polymeric material that is biodegradable or dissolvable in skin. In some embodiments, the microneedles comprise a mixture of a polymeric material and an active agent beneficial to skin.

Suitable polymeric materials include polymethylmethacrylate (PMMA), poly(glycolic acid-co-lactic acid) (PLGA), polyethylene (PE), polycaprolactone (PCL), polypropylene. The polymeric materials may comprise a glycosaminoglycans (GAG), such as hyaluronan, chondroitin, heparin, collagen, fibroin, elastin, various polysaccharides, cellulose derivatives, and the like. In some embodiments, the microneedles comprise a blend or combination of different polymers.

The beneficial agent may be any beneficial ingredient for improving skin, for example improving skin health, texture, hydration, or elasticity. Such agents include vitamins (for example, A, C, B), antioxidants, skin-whitening agents, peptides and growth factors.

In some embodiments, the polymeric material is a polysaccharide, for example, hyaluronic acid. In some embodiments, the beneficial agent and the polymeric material are both hyaluronic acid. In some embodiments, the polymeric material is a crosslinked polymer, for example, crosslinked hyaluronic acid. Crosslinking of hyaluronic acid may be accomplished in any suitable manner known to those of skill in the art.

To make the present microneedle devices, a precursor composition is provided, for example, a polymeric gel composition including, or without, one or more beneficial additives. The precursor composition may be made using known techniques for example, known techniques for making hyaluronic acid-based dermal filler gels. The gel may be formed into gel microneedles using, for example, micromolding technologies. The microneedles project from a substrate to facilitate handling. The substrate may be the same material as the microneedles, or may be a different material. The substrate may be any suitable flexible substrate, such as a fabric, sheet or membrane. The formed gel microneedles may be then be allowed to become, or may be caused to become, dried, hardened projections that will penetrate skin.

Hyaluronic acid is a non-sulfated glycosaminoglycan that enhances water retention and resists hydrostatic stresses. It is non-immunogenic and can be chemically modified in numerous fashions. Hyaluronic acid may be anionic at pH ranges around or above the pKa of its carboxylic acid groups. Unless clearly indicated otherwise, reference to hyaluronic acid, hyaluronan, or HA herein may include its fully protonated, or nonionic form as depicted below, as well as any anionic forms and salts of hyaluronic acid, such as sodium salts, potassium salts, lithium salts, magnesium salts, calcium salts, etc.

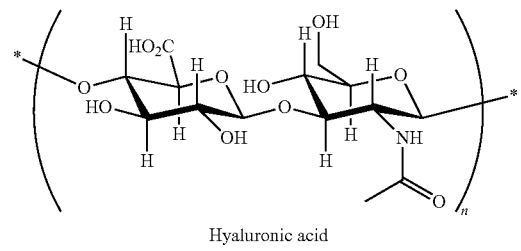

Hyaluronic acid

Figure 3A:
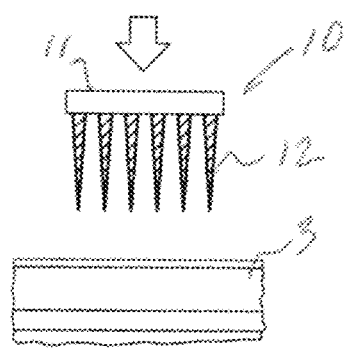
FIGS. 3a-3c illustrate, in simplified form, a mechanism of action of a microneedle device of an embodiment of the present invention.
Figure 3B:
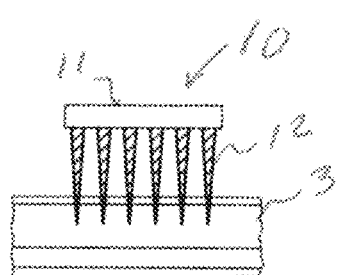
Figure 3C:
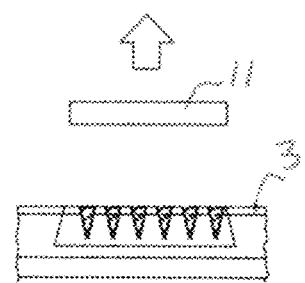

Turning now to FIGS. 3a-3c, in one aspect, a skin treatment device 10 is provided which allows for a "poke, dissolve and release" mechanism. For example, the device 10 may comprise a substrate 11, and an arrangement, for example, an array, of microneedles 12 projecting from the substrate 11 (FIG. 3a). The microneedles 12 comprise a polymeric component and an active pharmaceutical, drug or other beneficial agent. The agent may be combined with, mixed in, encapsulated, or crosslinked with or into, the polymer component. The microneedles 12 are structured to be capable of penetrating the skin 3 (FIG. 3b), for example, the epidermis, and are released in the tissues below the skin surface and dissolved (FIG. 3c). Dissolution of the polymeric component of the microneedle causes release of the beneficial agent into the skin, for example, as the polymer breaks down, biodegrades or dissolves.

Figure 4:
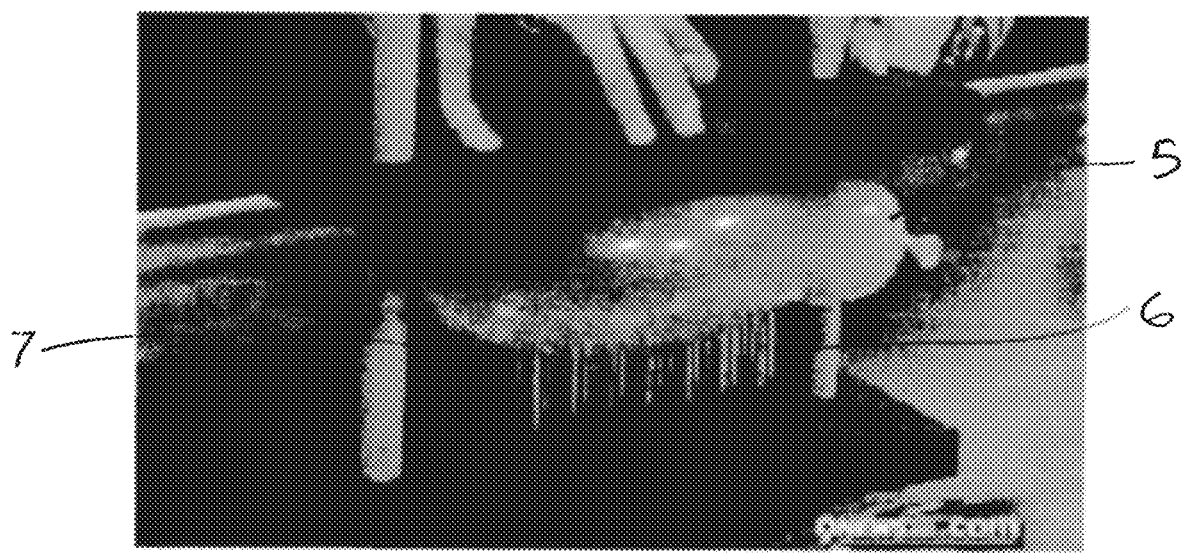
FIG. 4 shows a balloon representing skin, being pressed against an array of nails representing a PRIOR ART microneedle array.

One drawback with PRIOR ART microneedle technology, such as the microneedles shown with FIG. 1 described above is that all of the needles are of the same shape, length and are uniformly spaced apart. However, the natural elasticity of skin often prevents individual needles from effectively penetrating the skin. This concept is graphically illustrated in FIG. 4. An inflated balloon 5 is used to represent skin, and an array 6 of nails 7 with identical lengths is used to represent a prior art microneedle device having microneedles all of the same length. As illustrated, the nail tips are generally unable to penetrate or puncture through the balloon 5, or at least not without substantial pressures being applied between the balloon and the array of nails.

Figure 5A:
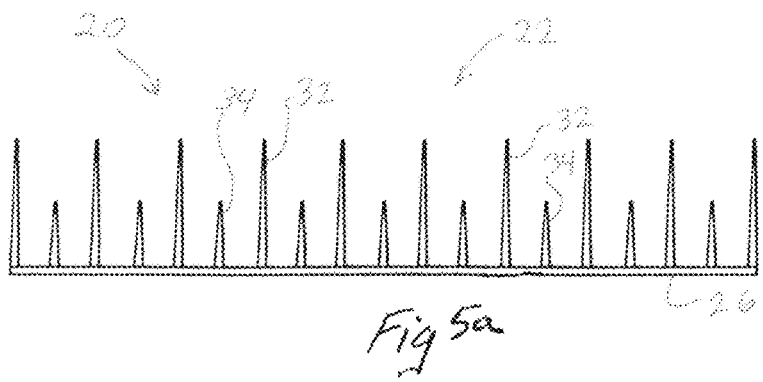
FIGS. 5a and 5b show, in simplified form, an array of microneedles in some embodiments of the invention, and penetration of skin thereby.
Figure 5B:
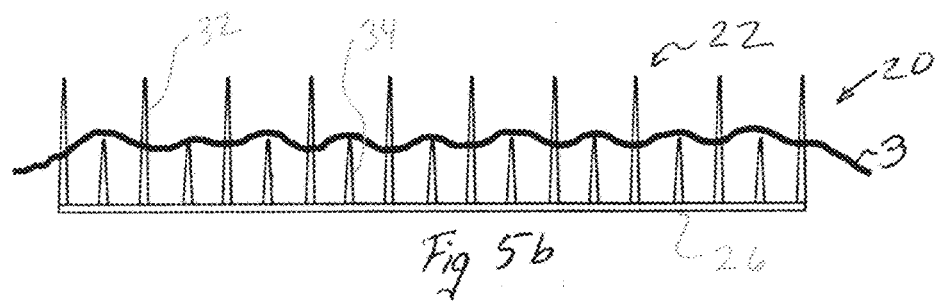

Advantageously, referring now to FIGS. 5a-5b, in some embodiments of the invention, a skin treatment device 20 is provided comprising a microneedle array 22 comprising microneedles projecting from a substrate 26. The microneedle array 22 comprises needles of differing or varying lengths (sometimes referred to as "heights." For example, the device 20 comprises first microneedles 32 having a first length and second microneedles 34 having a second length different from the first length. First microneedles 32 and second microneedles 34 may be disposed in an alternating fashion, for example, in ones, twos, threes, or more. The microneedles 32, 34 may be arranged in a set pattern or may be arranged randomly.

In some embodiments, the first length is at least about 1% greater in length than the second length. For example, in some embodiments, the first length is at least about 5%, at least about 10%, at least about 20%, at least about 30%, at least about 40%, at least about 50%, at least about 60%, at least about 70%, at least about 80%, at least about 90%, at least about 100%, at least about 150%, at least about 200%, at least about 300%, at least about 500%, at least about 800%, or at least about 1000% greater in length than the second length. In some embodiments, the first microneedles may have a length that is at least about 10% to about 200% greater than the length of the second microneedles. For example, the first microneedles have a length that is about 30%, or about 40%, or about 50%, or about 60%, or about 70%, or about 80%, or about 90%, or about 100%, or about 110%, or about 120%, or about 130%, or about 140%, or about 150%, or about 160%, or about 170%, or about 180%, or about 190%, or about 200% or greater than the length of the second microneedles.

The device 20 is structured to be more effective in penetrating skin 4, for example, relative to an otherwise identical PRIOR ART device 1 having needles all of the same length, such as described above. By alternating needle length, the pressure of individual tall needles, for example, needles 32, is increased and therefore potentially increases the number and amount of microneedles ultimately capable of penetrating the skin. This might be better appreciated by referring to FIG. 5b.

The microneedles 32, 34 may comprise a mixture of a polymeric material and an active agent beneficial to skin. The array 22 may be formed by molding the microneedles 32, 34 using conventional molding techniques.

Figure 6A:
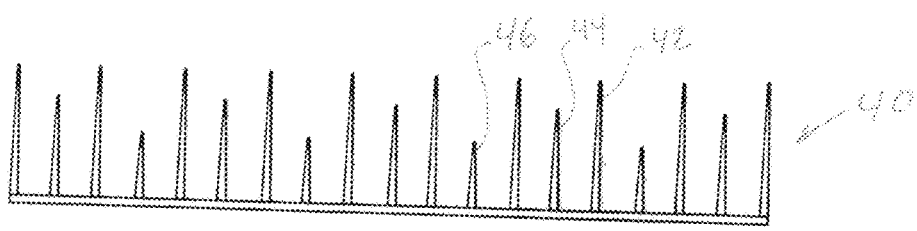
FIGS. 6a and 6b show, in simplified form, an array of microneedles in other embodiments of the invention, and penetration of skin thereby.
Figure 6B:
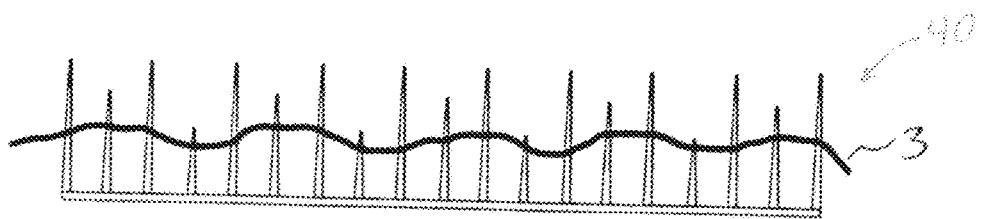

Another embodiment of the invention is shown in FIGS. 6a and 6b. In this case, a device 40, similar to device 20, is provided, which comprises array 41 comprising microneedles 42, 44, 46 of at least three or more different lengths.

It is known that different areas of the facial skin have different dermal thicknesses. For example, the tear troughs, that is, the skin directly under the eyes, have extremely thin dermal layers, while the chin region of the face has a relatively thick dermis. It is contemplated that by varying the multiple needle lengths, as described herein, various devices in accordance with the invention can be made which provide a desired penetration profile of selected facial areas.

In some embodiments of the invention, microneedles are provided which have a beneficial depth of penetration, depending upon the patient's age, skin type, and/or area of skin being treated. For example, in one aspect of the invention, a skin treatment device is provided which comprises a substrate having a first region including microneedles having a first length, and a second region adjacent the first region and including microneedles having a second length that is different from the first length.

Figure 7:
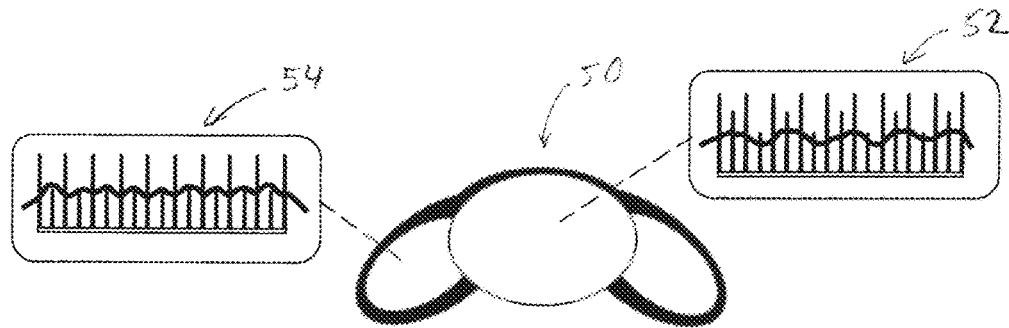
FIG. 7 shows yet another embodiment of the invention.

Turning now to FIG. 7, in another embodiment, a patch device 50 is provided that includes certain regions with particular needle arrays, which takes into account variances in dermal thicknesses of a patient. This may facilitate efficient drug delivery to various areas of the face, for example. For example, device 50 is in the form of a patch having array 52 for the nose bridge, and a different array 54 for the thinner facial region adjacent the nose. The device 50 is thus in the form of a single patch that is capable of effectively delivering drugs or beneficial agents to different regions of the skin, in this case, the nose bridge and the cheeks and/or tear trough, at a depth of penetration suitable for the skin region, based on the different arrangements of microneedles.

Generally, in order for microneedles to effectively dissolve and release within the skin to provide a benefit for skin rejuvenation, the depth of penetration may be between about 25 µm to about 2000 µm, for example, about 100 µm to about 1000 µm. In some embodiments, the microneedles have a length of less than 100 µm, and in some embodiments, the microneedles have a length of greater than 1000 µm, for example, up to about 2000 µm. In some embodiments, the microneedles, for example, the longest microneedles in the arrangement, have a length of between about 200 µm and about 600 µm, for example, about 400 µm, or even more specifically, about 420 µm to about 480 µm.

In one embodiment, a skin treatment device in accordance with the invention comprises a substrate and spaced apart hyaluronic acid-based microneedles projecting from the substrate, wherein the microneedles have a length of between about 420 µm and 480 µm, a base of between about 200 µm and about 300 µm, for example, a base of about 270 µm, and a tip width of less than 20 µm, for example, a tip width of about 5 µm.

For use in the tear trough region, in one embodiment, the microneedles, for example, the first microneedles, have a length less than about 500 µm, for example, between about 100 µm to about 500 µm, for example, a length of about 400 µm, for example, a length of about 300 µm, for example, a length of about 200 µm. For use in the chin region, the microneedles have a length greater than about 500 µm, for example, a length of between about 500 µm to about 2000 µm, for example, a length of about 600 µm, for example, a length of about 700 µm, for example, a length of about 800 µm, for example, a length of up to about 1000 µm, of up to about 2000 µm.

In another embodiment, the first microneedles have a length of about 1000 µm and the second microneedles have a length of about 500 µm. For example, the first microneedles may be in the region of the patch for application on the nose of the patient, where the skin in relatively thick, and the second microneedles may be in a region of the patch that is intended for the regions of skin directly adjacent the nose, where the skin is relatively thin.

In other embodiments, the first microneedles have a length of about 800 μm and the second microneedles have a length of about 200 μm. In yet another embodiment, the first microneedles have a length of about 500 μm and the second microneedles have a length of about 300 μm.

It is further contemplated that the device may comprise microneedles having a third length different from the first and second length, and a fourth length different from the first second and third lengths.

Spacing between adjacent microneedles may be uniform or non-uniform across the microneedle arrangement. For example, in some embodiments, spacing between microneedles is substantially uniform. Spacing may be between about 100 μm and about 2000 μm, for example, 200 μm, about 300 μm, about 400 μm, about 500 μm, about 600 μm, about 700 μm, about 800 μm, about 900 μm, about 1000 μm, about 1100 μm, about 1200 μm, about 1300 μm, about 1400 μm, about 1500 μm, about 1600 μm, about 1700 μm, about 1800 μm, about 1900 μm, or about 2000 μm, or greater, between adjacent microneedles.

Figure 8:
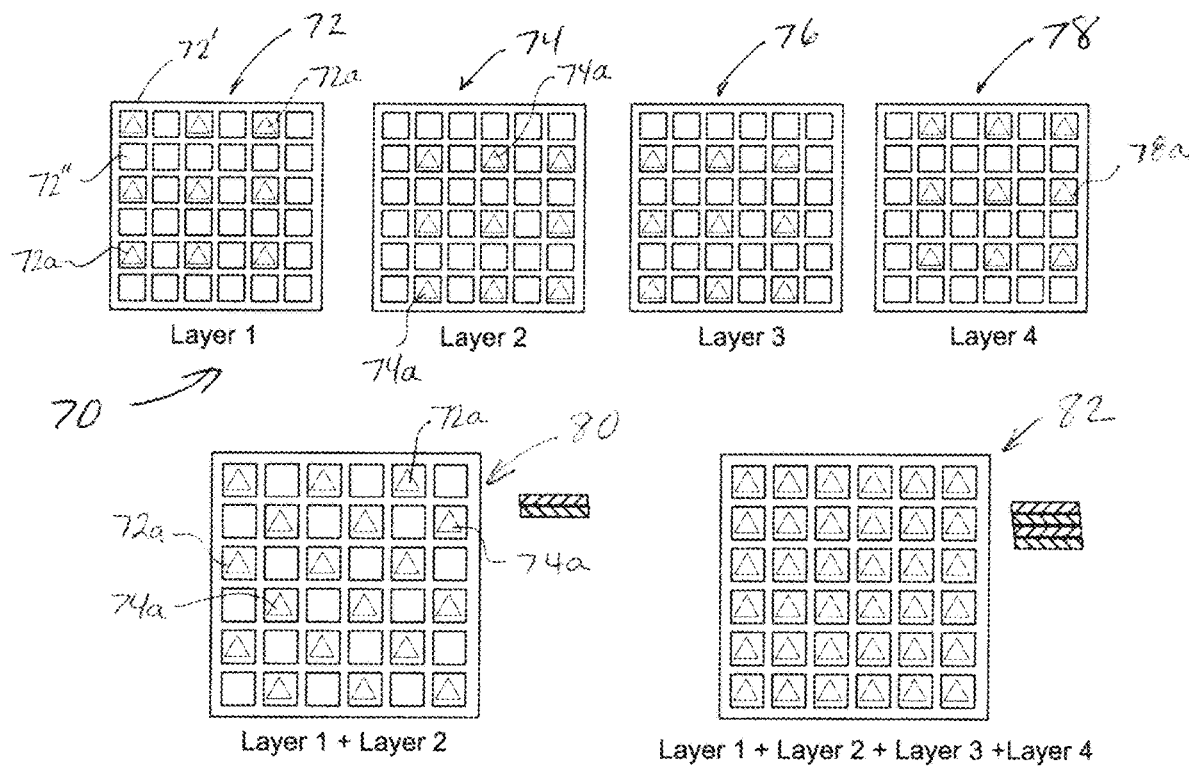
FIG. 8 illustrates an assembly in accordance with some embodiments of the invention, useful for treating skin using layered microneedle devices.

In yet another embodiment, illustrated in FIG. 8, the present invention provides a skin treatment device 70 comprising a plurality of stages, or layers 72, 74, 76, 78. The layers 72, 74, 76, 78 may be designed to be applied to the skin in an overlapping fashion. The device 70 provides custom treatment for a patient depending upon the type of skin, or the amount or type of active agent to be delivered. For example, device 70 may be used to create different layered microneedle patches 80, 82, each tailored to a patient's unique skin qualities.

Each of the layers, for example, layer 72, may comprise a substrate 72 having spacing or perforations 72 and microneedles 72a located generally between the spacing 72". The needles 72a may be throttled to permit a number of layers to be stacked on one another, with needles of adjacent layers extending in the spacing between needles of other adjacent layers.

For example, for use in a patient having a rougher, more deflective skin, layered patch 80 comprising fewer layers 72, 74, and thus a lower density of needles, may be utilized to treat the skin. For a patient having a relatively softer skin, a patch 82 comprising more layers, such as layers 72, 74, 76 and 78, and thus a higher density of needles, could be used to treat the skin. For example, a single layer, for example, layer 72 may be used for treatment of a patient having rough, more deflective skin. A layered patch 80, comprising a combination of layer 72 and layer 74, may be used for treatment of a patient having semi-rough, less deflective skin. A patient with relatively smooth skin may be treated with a denser needle array, for example, a layered patch 82 comprising a combination of layers 72, 74, 76 and 78.

The layers 72, 74, 76, 78 could be pre-assembled before being applied to the skin, or could be layered during a treatment session while on the skin.

In some embodiments, each of layers 72, 74, 76 and 78 comprises a different specific needle length, such that when the layers are placed together, the assembly provides a desired treatment profile.

For example, layer 72 may include only relatively long needles 72a and layer 78 may comprise only relatively short needles 78a. In some embodiments, each layer comprises needles of appropriate needle length to effectively deliver an equivalent amount of active agent per needle.

In some embodiments, each of layers 72, 74, 76 and 78 comprises a different, specific pharmaceutical, or other beneficial agent, such that when the layers are placed together, the assembly provides a desired treatment profile, for example, made up of a combination of such agents.

For example, layer 72 may include needles 72a comprising hyaluronic acid and Vitamin C as an active agent, while layer 74 includes needles 74a having hyaluronic acid and Vitamin E as an active agent. Thus, patch 80, comprising layered 72 and 74, can be used to deliver both hyaluronic acid, Vitamin C and Vitamin E.

Figure 9:
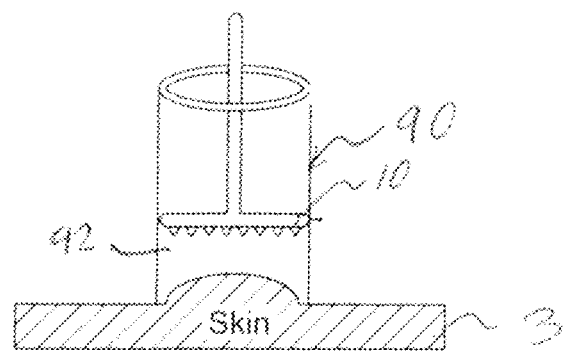
FIGS. 9 and 10 illustrate, in simplified form, embodiments of the invention using negative pressure to enhance effectiveness of the present invention.

In yet another embodiment, as show in simplified form in FIG. 9, a method of treating skin is provided. The method comprises drawing an area of skin 3 to be treated toward a microneedle device, for example, device 10, or any other microneedle device in accordance with the invention as described elsewhere herein. The method comprises using negative pressure, for example by means of a vacuum mechanism 90 having vacuum chamber 92, in order to stretch the skin and enhance penetration of microneedles into the skin 3. This method reduces deflection of the skin away from the needles and improves the number of needles that penetrate the skin and/or depth of needle penetration.

Any suitable vacuum or negative pressure mechanism may be used to accomplish more effective needle penetration in accordance with this embodiment. For example, in one embodiment, the vacuum mechanism 90 includes essentially no moving parts, and vacuum chamber 92 supplies negative pressure to draw the surface of skin 3 toward microneedle device 10. The microneedle device 10 can be flexibly sealed against the walls of the chamber such as by means of a rubber or other suitable material gasket, thus allowing the device 10 to move toward skin while maintaining a vacuum.

Figure 10:
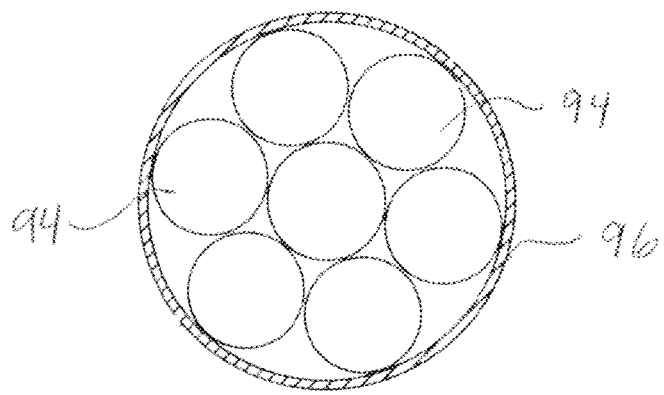

As depicted in FIG. 9, the skin 3 may experience maximum deflection in the central area within the vacuum chamber 92. It is contemplated that in order to compensate for uneven deflection, the microneedles at the perimeter of the device 10 can be made longer than the needles in the inner portion thereof. Another means to address uneven skin deflection caused by the vacuum is to provide an appropriately sized vacuum area so that the micro-needle penetration area is sufficient for therapeutic coverage but small enough to permit consistency. For example, as illustrated in FIG. 10, multiple vacuum chambers 94, for example, seven vacuum chambers, located within a single housing 96, may be used to provide more consistent needle penetration and to enable coverage of a larger skin area in single application.

Figure 11:
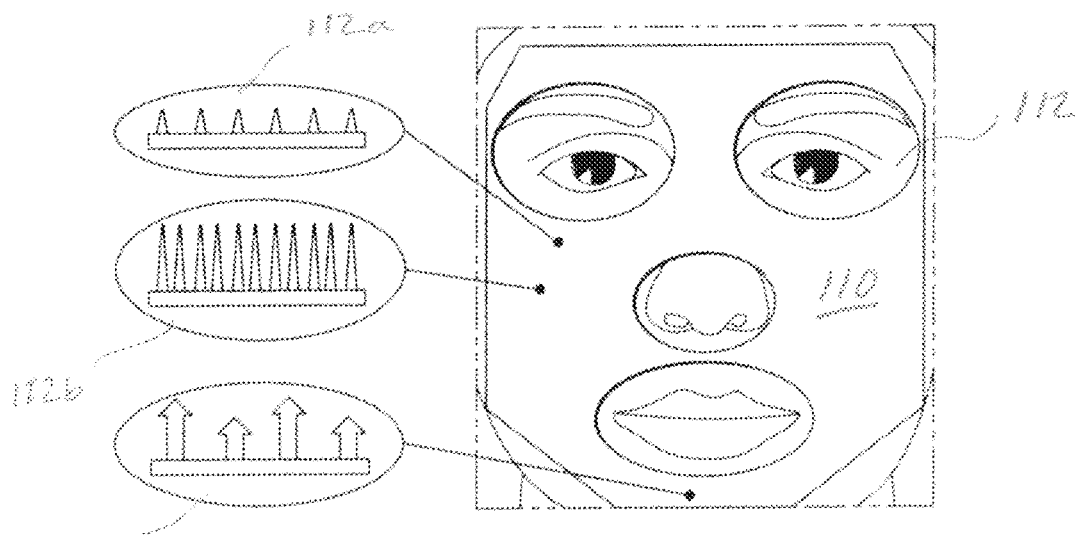
FIGS. 11, 12 and 13 illustrate yet other embodiments of the invention.

Turning now to FIG. 11, in yet another embodiment of the invention, device 110 of the invention is in the form of a stretchable mask. Device 110 may be similar to devices 10, 20, 40, 50, 70, 80 and 82, and may include one or more of the features already described. Device 110 may have substrate in a generic face shape, for example, with cutouts 112 for the eyes, lips, and/or and any other areas. Either the substrate only, or the entire device 110 including the microneedles, can be made of a stretchable material. As illustrated, arrangements of microneedles of the device 110 can be different for treating different locations of the face. For example, the needle length, density of needles, or needle geometry can be altered depending on the region of the face they are intended to treat. For example, microneedles 112a are provided for treatment below the eye, microneedles 112b are provided for treatment of the cheek region, and microneedles 112c are provided for treatment of the chin region.

Figure 12:
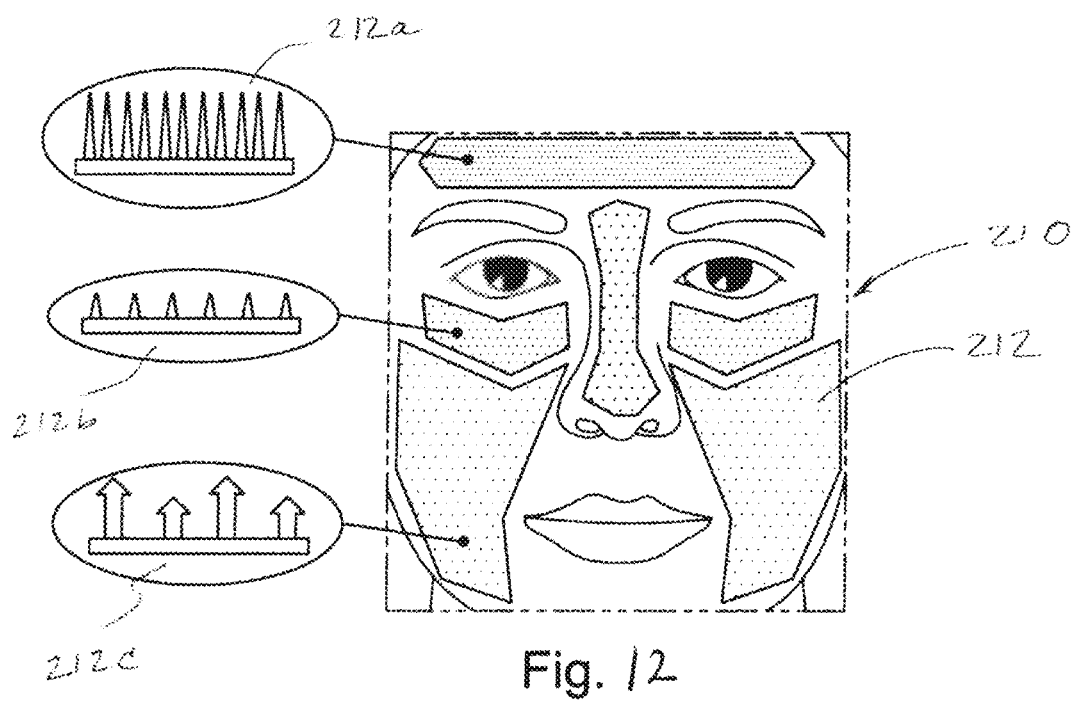

Alternatively, turning now to FIG. 12, instead of one large mask-like device such as shown in FIG. 11, in some embodiments, device 210 is provided which comprises separate, discrete patches 212 are provided for specific areas of the face. This is illustrated in FIG. 12. The ability of the discrete patches to overlap allows the patches to accommodate many potential face shapes and sizes. In this embodiment, area specific microneedle patches are applied independently across a patient's face. Each patch may include the same or different arrangements of microneedles, for example, arrangements 212a, 212b, 212c. For example, the needle length, density of needles, type or dosage of beneficial agent, or even needle geometry can be altered depending on where on the region of the face they will be used to treat.

Figure 13:
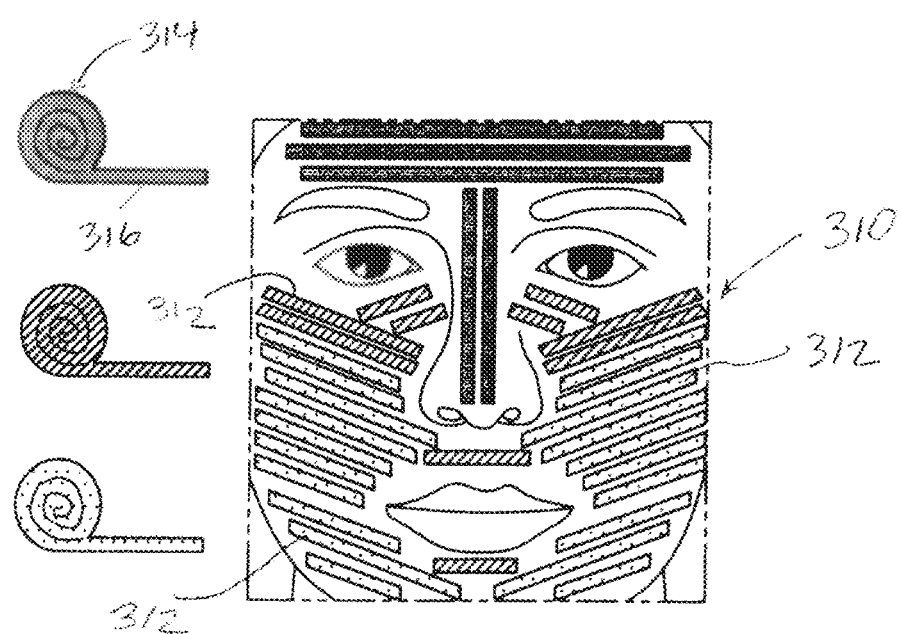

Another embodiment, illustrated in FIG. 13, is provided which generally comprises an assembly 310 comprising microneedle strips 312 which may be applied to skin in rows, or other patterns, to obtain the precise coverage desirable for a patient. Such strips 312 may be provided in the form of a roll 314 of tape 316. The tape 316 may have features that indicate which side of the tape contains the microneedles. This may be a color, text, or shape indication. This embodiment allows rapid large surface area application over a wide variety of patient anatomies.

Similar to unique needle geometries among the face specific patch embodiments, several strip "types" may be provided that can be used during a single procedure. Each strip may be used on specific areas of the face, with needles on each strip with unique needle length, density of needles, needle geometry, etc. The microneedle geometries may be unique to specific "tapes" to be applied on certain regions of the face.

EXAMPLE

Preparation of Microneedle Device in Accordance with an Embodiment, Using Hyaluronic Acid (HA)

Preparation of HA Gel Hydrate:

HA gel hydrates were made by hydrating low molecular weight (LMW) HA (Mw is about 340,000 to about 840,000 Da) in deionized (DI) water or phosphate buffered saline (PBS). For a 12 wt % of LMW HA, approximately 1.20 g of LMW HA and 8.80 g of DI water were mixed in a 20 mL syringe. The mixture was left at room temperature for 24 hours to achieve a uniform hydrogel. The gel was then transferred to a 1.0 mL syringes and centrifuged at 4000 rμm for 5.0 min.

HA Gel Casting:

The casting of HA gel includes two steps, casting and pre-concentrating. In the casting step, HA gel was cast on the negative silicone microneedle mold and upon evaporation of water at room temperature or in an oven, the solution formed a viscous paste on the top of the mold. For example, 0.65 mL of a 12 wt % HA gel was cast onto the center of the negative silicone mold. The gel together with the silicone mold was placed into an oven which was pre-set at 40° C. After 1.50 hours of incubation, the gel formed a paste and was removed from the oven for the compression step.

Pressing and Post-Incubation:

The HA paste together with the negative silicone microneedle mold was placed on a compressor. A PTFE film was placed on top of the HA paste. The compression pressure was set to 20 psi initially, then increased to 50 psi at a constant rate over a period of 30 seconds and held at this pressure for another 30 seconds.

Needle Formation:

After pressing, the PTFE film was removed and a flat layer of HA remained on top of the mold. The mold was then placed into a 40° C. oven for 2.5 hours. The dried microneedle batch was then removed from the mold and sent for characterizations by SEM and x-ray CT.

Although the various embodiments of the invention have been described and illustrated with a certain degree of particularity, it is understood that the present disclosure has been made only by way of example, and that numerous changes in the combination and various arrangement of parts, features and components can be resorted to by those skilled in the art without departing from the scope of the invention, as hereinafter claimed.

What is claimed is:

1. A method for manufacturing a microneedle device comprising the steps of:
   providing a precursor composition comprising a hyaluronic acid (HA) gel hydrate;
   casting the precursor composition onto a negative microneedle mold, the mold defining a microneedle array;
   partially dehydrating the precursor composition to provide a pre-concentrated composition;
   compressing the pre-concentrated composition;
   drying the pre-concentrated composition thereby forming a solid microneedle array; and
   removing the solid microneedle array from the negative microneedle mold.

2. The method of claim 1, wherein the step of providing a precursor composition comprises mixing a HA in an aqueous medium to form a mixture and allowing the mixture to equilibrate, thereby forming a uniform hydrogel.

3. The method of claim 2, wherein the HA is a low molecular weight HA having a molecular weight in the range of about 340,000 Da to about 840,000 Da.

4. The method of claim 2, wherein the aqueous medium is selected from deionized water and phosphate buffered saline (PBS).

5. The method of claim 2, wherein the HA is selected from the group consisting of a fully protonated hyaluronic acid; a deprotonated hyaluronic acid; a salt of hyaluronic acid; and combinations thereof.

6. The method of claim 1, wherein the step of partially dehydrating the precursor composition comprises evaporation of water at room temperature.

7. The method of claim 1, wherein the step of partially dehydrating the precursor composition comprises incubating the HA gel hydrate and negative microneedle mold in an oven.

8. The method of claim 7, wherein the oven has been preheated.

9. The method of claim 7, wherein the incubating is performed at a temperature of 40° C.

10. The method of claim 7, wherein the incubating is performed for a period of about 1.5 hours.

11. The method of claim 1, wherein the negative microneedle mold is a silicone mold.

12. The method of claim 1, wherein the negative microneedle mold is configured to produce a microneedle array comprising microneedles having a length of about 25 μm to about 2000 μm.

13. The method of claim 1, wherein the negative microneedle mold is configured to produce a microneedle array comprising first microneedles having a first length and second microneedles having a second length different from the first length, wherein in a side view, the first microneedles are arranged with the second microneedles along a substrate in a set pattern, the first microneedles having a length of between 200 μm and 2000 μm.

14. The method of claim 13, wherein the set pattern consists of the first and second microneedles arranged in an alternating fashion.

15. The method of claim 1, wherein the step of compressing the pre-concentrated composition comprises applying a film on top of the pre-concentrated composition prior to compressing the pre-concentrated composition.

16. The method of claim 15, wherein the step of compressing the pre-concentrated composition comprises applying an initial compression pressure, incrementally increasing the compression pressure at a constant rate until a predetermined maximum compression pressure is achieved, and maintaining the compression pressure at the predetermined maximum pressure for a period of time.

17. The method of claim 16, wherein the initial compression pressure is 20 psi, the predetermined maximum compression pressure is 50 psi, and the period of time is about 30 seconds.

18. The method of claim 1, wherein the step of drying the pre-concentrated composition comprises incubating at 40° C. for about 2.5 hours.

19. The method of claim 1, wherein the precursor composition further comprises an active agent beneficial to skin.

20. The method of claim 19, wherein the active agent is selected from the group consisting of vitamins, antioxidants, skin-whitening agents, peptides, and growth factors.

* * * * *